(12) United States Patent
Kim et al.

(10) Patent No.: US 8,301,244 B2
(45) Date of Patent: Oct. 30, 2012

(54) SUSTAINING VENTRICULAR TACHYCARDIA DETECTION

(75) Inventors: Jaeho Kim, Redmond, WA (US); Dan Li, Shoreview, MN (US); Joseph M. Bocek, Seattle, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 501 days.

(21) Appl. No.: 12/552,614

(22) Filed: Sep. 2, 2009

(65) Prior Publication Data
US 2010/0057152 A1   Mar. 4, 2010

Related U.S. Application Data

(60) Provisional application No. 61/094,217, filed on Sep. 4, 2008.

(51) Int. Cl.
*A61B 5/046* (2006.01)
(52) U.S. Cl. ............................. 607/4; 600/518
(58) Field of Classification Search .............. 607/4, 9, 607/14; 600/508, 509, 515, 518
See application file for complete search history.

(56) References Cited

U.S. PATENT DOCUMENTS

| | | | |
|---|---|---|---|
| 5,379,776 | A | 1/1995 | Murphy et al. |
| 6,076,014 | A | 6/2000 | Alt |
| 6,190,324 | B1 | 2/2001 | Kieval et al. |
| 6,493,579 | B1 | 12/2002 | Gilkerson et al. |
| 6,522,925 | B1 | 2/2003 | Gilkerson et al. |
| 6,708,058 | B2 | 3/2004 | Kim et al. |
| 6,873,870 | B2 | 3/2005 | Ferek-Petric |
| 6,889,081 | B2 | 5/2005 | Hsu |
| 7,120,491 | B1 | 10/2006 | Bailin et al. |
| 7,184,818 | B2 | 2/2007 | Kim et al. |
| 7,774,062 | B2 * | 8/2010 | Kim et al. ............... 607/14 |
| 2004/0088013 | A1 | 5/2004 | Stadler et al. |
| 2007/0135848 | A1 | 6/2007 | Kim et al. |
| 2007/0135852 | A1 | 6/2007 | Kim et al. |
| 2007/0197928 | A1 | 8/2007 | Kim et al. |
| 2010/0298902 | A1 | 11/2010 | Kim et al. |

OTHER PUBLICATIONS

"U.S. Appl. No. 11/301,440, Response filed Dec. 2, 2009 to Non-Final Office Action mailed Aug. 10, 2009", 11 pgs.
"U.S. Appl. No. 11/301,440, Restriction Requirement mailed Mar. 31, 2009", 8 pgs.
"U.S. Appl. No. 11/301,440, Response and Preliminary Amendment filed Apr. 30, 2009 to Restriction Requirement mailed Mar. 31, 2009", 10 pgs.
"U.S. Appl. No. 11/301,440, Non-Final Office Action mailed Aug. 10, 2009", 5 pgs.
"U.S. Appl. No. 11/301,440, Notice of Allowance mailed Mar. 25, 2010", 9 pgs.
"U.S. Appl. No. 12/849,714, Non-Final Office Action mailed Jun. 11, 2012", 6 pgs.

* cited by examiner

*Primary Examiner* — Eric D. Bertram
(74) *Attorney, Agent, or Firm* — Schwegman Lundberg & Woessner, P.A.

(57) ABSTRACT

An apparatus comprises an implantable ventricular depolarization sensing circuit configured to provide a sensed ventricular depolarization signal, a timer circuit configured to provide a ventricular time interval between ventricular depolarizations, and a controller circuit communicatively coupled to the ventricular depolarization sensing circuit and the timer circuit. The controller circuit includes a ventricular tachycardia (VT) detection circuit configured to declare an episode of VT when a number of accelerated beats are detected, calculate a hysteresis VT detection threshold interval, and deem whether the episode of VT persists using the hysteresis VT detection threshold interval.

21 Claims, 4 Drawing Sheets

SUSTAINING VENTRICULAR TACHYCARDIA DETECTION

CLAIM OF PRIORITY

This non-provisional application claims the benefit of priority under 35 U.S.C. §119(e) to U.S. Provisional Patent Application Ser. No. 61/094,217, filed Sep. 4, 2008, the specification of which is herein incorporated by reference in its entirety.

BACKGROUND

Implantable medical devices (IMDs) include devices designed to be implanted into a patient or subject. Some examples of these devices include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients using electrical or other therapy, or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of implantable medical devices include implantable diagnostic devices, implantable drug delivery systems, or implantable devices with neural stimulation capability.

Additionally, some IMDs detect events by monitoring electrical heart activity signals. In CFM devices, these events can include heart chamber expansions or contractions. By monitoring cardiac signals indicative of expansions or contractions, IMDs can detect abnormally slow heart rate, or bradycardia. The monitoring can also be used to verify that electrical pacing therapy resulted in depolarization of a heart of a subject (e.g., used for sensing an evoked response).

Some IMDs detect abnormally rapid heart rate, such as tachyarrhythmia. Tachyarrhythmia includes ventricular tachycardia (VT) which originates from the ventricles. Tachyarrhythmia also includes rapid and irregular heart rate, or fibrillation, including ventricular fibrillation (VF). Abnormally rapid heart rate can also be due to supraventricular tachycardia (SVT). SVT is less dangerous to the patient than VT or VF. SVT includes arrhythmias such as atrial tachycardia, atrial flutter, and atrial fibrillation. A rapid heart rate can also be due to sinus tachycardia, which is a normal response to exercise or an elevated emotional state.

Typically, ICDs detect tachyarrhythmia by first detecting a rapid heart rate. When detected, ventricular tachyarrhythmia can be terminated using high-energy shock therapy. Other detection methods in addition to fast rate detection are used to reduce the incidence of inappropriate shocks. It is important for IMDs to quickly and accurately classify sensed rhythms or arrhythmias and deliver the appropriate therapy.

OVERVIEW

This document relates generally to systems, devices, and methods for monitoring cardiac electrophysiological parameters of a patient or subject. Episodes of ventricular tachyarrhythmia are also monitored. In example 1, an apparatus includes an implantable ventricular depolarization sensing circuit configured to provide a sensed ventricular depolarization signal, a timer circuit configured to provide a ventricular time interval between ventricular depolarizations, and a controller circuit communicatively coupled to the ventricular depolarization sensing circuit and the timer circuit. The controller circuit includes a ventricular tachycardia (VT) detection circuit configured to declare an episode of VT when a number of accelerated beats are detected. An accelerated beat concludes a ventricular time interval having a shorter duration than a specified central tendency of previous ventricular time intervals. The VT detection circuit also calculates a hysteresis VT detection threshold interval using an accelerated beat interval and a non-accelerated beat interval detected after the VT onset, and deems whether the episode of VT persists using the hysteresis VT detection threshold interval.

In example 2, the VT detection circuit of example 1 optionally determines an estimated onset ventricular time interval using a value of at least one accelerated beat interval when the episode of VT is declared, determines an estimated end ventricular time interval using a value of at least one non-accelerated beat interval when a specified number of non-accelerated beat intervals are detected after the episode of VT is declared, and calculates the hysteresis VT detection threshold interval using the estimated onset ventricular time interval and the estimated end ventricular time interval.

In example 3, the VT detection circuit of examples 1 and 2 optionally determines an onset central tendency ventricular time interval using a value of a running central tendency beat interval when VT is declared, determines an end central tendency ventricular time interval using the value of the running central tendency beat interval when a specified number of non-accelerated beat intervals are detected after the VT is declared, and calculates a hysteresis VT detection threshold interval that is between the onset central tendency ventricular time interval and the end central tendency ventricular time interval.

In example 4, the hysteresis VT detection threshold interval of examples 1-3 is optionally an average of an onset average ventricular time interval and an end average ventricular time interval.

In example 5, the VT detection circuit of examples 1-4 optionally determines a ventricular depolarization rate from ventricular time intervals, detects the episode of VT when the ventricular depolarization rate exceeds a VT detection threshold rate, and when the ventricular depolarization rate exceeds the VT detection threshold rate, deems whether the episode of VT persists using a rate corresponding to the calculated hysteresis VT detection threshold interval instead of using the VT detection threshold rate, and when the ventricular depolarization rate is less than the VT detection threshold rate, deems whether the episode of VT persists using the VT detection threshold rate.

In example 6, the VT detection circuit of examples 1-4 optionally declares VT in response to detecting a sudden rate increase, without comparing a ventricular rate or time interval to a respective tachycardia detection rate or time interval threshold, wherein the sudden rate increase includes a specified number of accelerated beats occurring within a specified time period.

In example 7, the apparatus of examples 1-6 optionally includes an implantable atrial depolarization sensing circuit to provide a sensed atrial depolarization signal and the timer circuit provides an atrial time interval between atrial depolarizations, and wherein the VT detection circuit determines that at least one of an episode of VT is detected or a VT episode persists, when an average ventricular depolarization rate exceeds an average atrial depolarization rate by more than a specified rate threshold value.

In example 8, the VT detection circuit of examples 1-5 and 7 optionally first detects the episode of VT when a ventricular depolarization rate exceeds a VT detection threshold rate.

In example 9, the apparatus of claim 1 optionally includes a memory circuit communicatively coupled to the controller circuit, wherein at least one area of the memory circuit is allocated to store at least one of a normal sinus rhythm (NSR) template morphology or a supraventricular conducted rhythm (SVR) template morphology. The VT detection circuit determines that at least one of an episode of VT is detected or a VT episode persists using a comparison of a morphology of a sensed cardiac signal to the stored template morphology.

In example 10, the VT detection circuit of examples 1-9 optionally determines a measure of ventricular rhythm stability using ventricular time intervals and determines, using the measure of ventricular rhythm stability, that at least one of an episode of VT is detected or a VT episode persists.

In example 11, the apparatus of claims 1-10 optionally includes a therapy circuit, communicatively coupled to the controller circuit, to provide electrical anti-tachycardia therapy to the subject. The controller circuit initiates anti-tachycardia pacing (ATP) upon detecting the episode of sudden onset VT, and initiates at least one of modified ATP or defibrillation/cardioversion shock therapy upon deeming that the episode of VT persists using the hysteresis VT detection threshold interval.

In example 12, the apparatus of examples 1-11 optionally includes a communication circuit, communicatively coupled to the controller circuit, to communicate with an external device. The controller circuit is communicate an indication of the episode of VT to an external device upon deeming, using the hysteresis VT detection threshold interval, that the episode of VT persists longer than a specified time threshold.

In example 13, the apparatus of claims 1-10 and 12 optionally includes a therapy circuit communicatively coupled to the controller circuit. The therapy circuit provides at least one of defibrillation shock therapy and cardioversion shock therapy to the subject, and the controller circuit initiates a shock therapy upon detecting the episode of sudden onset VT.

In example 14, a method includes monitoring ventricular depolarization intervals (V-V intervals), between successive ventricular depolarizations, of a subject, declaring an episode of ventricular tachyarrhythmia (VT) at least in part from a number of detected accelerated beats (an accelerated beat is a ventricular time interval having a shorter duration than a specified central tendency of previous V-V intervals), determining a hysteresis VT detection threshold interval using an accelerated beat interval and non-accelerated beat interval that is detected after VT is declared, and deeming whether the episode of VT persists using the hysteresis VT detection threshold interval.

In example 15, the method of example 14 optionally includes detecting a specified number of accelerated beats, determining an onset central tendency V-V interval using at least one accelerated beat interval, and determining an end central tendency V-V interval using at least one non-accelerated beat interval that occurs a specified number of non-accelerated beat intervals after detecting the specified number of accelerated beats. The determining the hysteresis VT detection threshold interval optionally includes determining a hysteresis VT detection threshold interval that is between the onset central tendency V-V interval and the end central tendency V-V interval.

In example 16, the detecting an episode of VT of examples 14 and 15 optionally includes using a fixed VT detection threshold rate to detect the episode of VT and detecting a ventricular depolarization rate in the V-V intervals that is within a specified range of the fixed VT detection threshold rate. The deeming whether the episode of VT persists optionally includes using the hysteresis VT detection threshold interval, instead of the fixed VT detection threshold rate, to deem whether the episode of VT persists.

In example 17, the detecting an episode of VT of examples 14 and 15 optionally includes detecting a sudden rate increase in the V-V intervals without comparing a ventricular rate or time interval to a respective tachycardia detection rate or time interval detection threshold, wherein the sudden rate increase includes a specified number of accelerated beats, and wherein an accelerated beat is a V-V interval having a shorter duration than an average of previous V-V intervals, and the determining the hysteresis VT detection threshold interval includes calculating the hysteresis VT detection threshold interval using at least one accelerated beat interval.

In example 18, the determining the hysteresis VT detection threshold interval of examples 14-17 optionally includes determining a hysteresis VT detection threshold interval that is an average of an onset average ventricular time interval and an end average ventricular time interval.

In example 19, the declaring an episode of VT of examples 14-18 optionally includes at least one of: determining that an average ventricular depolarization rate exceeds an average atrial depolarization rate by more than a specified rate threshold value, comparing a morphology of a sensed cardiac signal to a template morphology or assessing the stability of the ventricular rhythm.

In example 20, the deeming whether the episode of VT persists of examples 14-19 optionally includes at least one of: determining that an average ventricular depolarization rate exceeds an average atrial depolarization rate by more than a specified rate threshold value, comparing a morphology of a sensed cardiac signal to a template morphology, or assessing the stability of the ventricular rhythm.

In example 21, the method of examples 14-20 optionally includes providing ATP upon detecting the episode of sudden onset VT, and providing at least one of modified ATP or defibrillation/cardioversion shock therapy upon deeming that the episode of VT persists using the hysteresis VT detection threshold interval.

In example 22, the method of examples 14-21 optionally includes communicating an indication of the episode of VT to an external device upon deeming, using the hysteresis VT detection threshold interval, that the episode of VT persists longer than a specified time threshold.

In example 23, the declaring an episode of VT of examples 14-22 optionally includes declaring an episode of sudden onset VT, and the deeming whether the episode of VT persists optionally includes deeming whether the episode of sudden onset VT persists using the hysteresis VT detection threshold interval.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

An implantable medical device (IMD) may include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions.

The present application discusses, among other things, systems and methods for detecting ventricular tachyarrhythmia. When VT is detected, IMDs are designed to provide therapy to the patient. ICDs treat VT by delivering a high energy electrical shock to the heart. Other IMDs provide anti-tachycardia pacing (ATP). ATP uses lower energy pacing energy to establish a regular rhythm in a heart. This allows the tachycardia to be converted to a normal heart rhythm without exposing the patient to high energy defibrillation therapy that can be painful to the patient.

Some IMDs are able to provide both ATP and defibrillation. When tachycardia is detected, the device may try to convert the arrhythmia with ATP before resorting to high energy defibrillation. After delivery of ATP therapy, it is important to quickly determine if the tachycardia still persists or whether the tachycardia has been converted to a normal heart rhythm.

Figure 1:
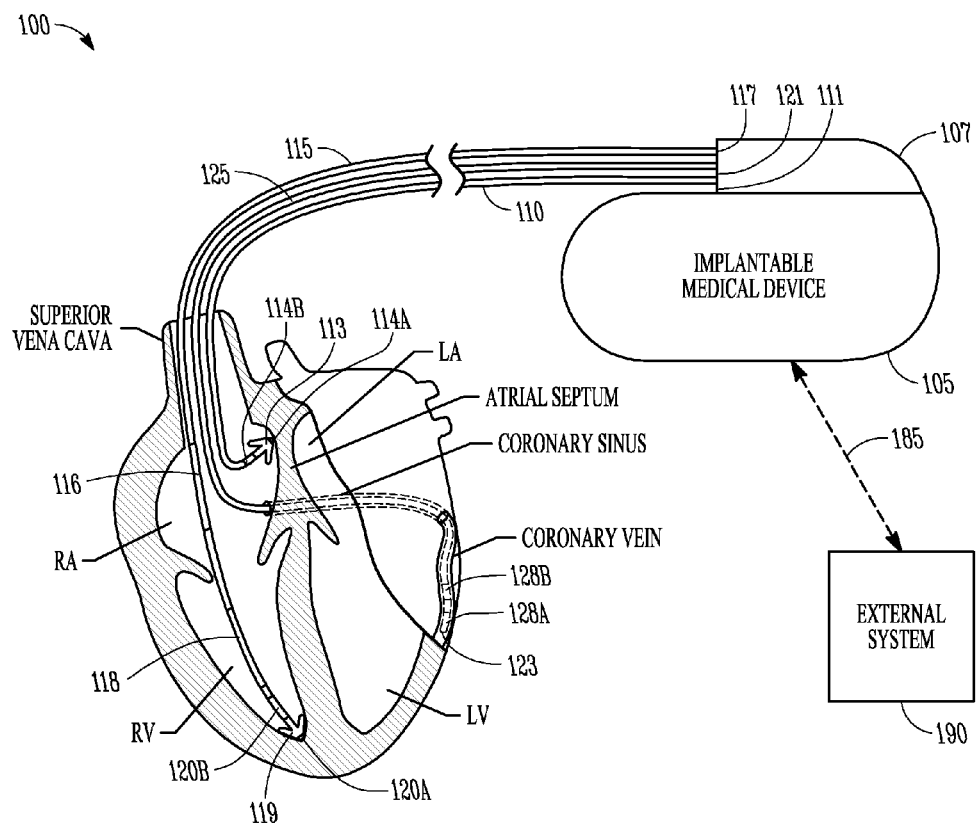
FIG. 1 is an illustration of portions of a system that uses an IMD.

FIG. 1 is an illustration of portions of a system 100 that uses an IMD 105. Examples of IMD 105 include, without limitation, a pacemaker, a cardioverter, a defibrillator, a cardiac resynchronization therapy (CRT) device, and other cardiac monitoring and therapy delivery devices, including cardiac devices that include or work in coordination with one or more neuro-stimulating devices, drugs, drug delivery systems, or other therapies. As one example, the system 100 shown is used to treat a cardiac arrhythmia. The IMD 105 typically includes an electronics unit coupled by one or more cardiac leads 110, 115, 125, to a heart of a patient or subject. The electronics unit of the IMD 105 typically includes components that are enclosed in a hermetically-sealed canister or "can." The system 100 also typically includes an IMD programmer or other external system 190 that communicates one or more wireless signals 185 with the IMD 105, such as by using radio frequency (RF) or by one or more other telemetry methods.

The example shown includes right atrial (RA) lead 110 having a proximal end 111 and a distal end 113. The proximal end 111 is coupled to a header connector 107 of the IMD 105. The distal end 113 is configured for placement in the RA in or near the atrial septum. The RA lead 110 may include a pair of bipolar electrodes, such as an RA tip electrode 114A and an RA ring electrode 114B. The RA electrodes 114A and 114B are incorporated into the lead body at distal end 113 for placement in or near the RA, and are each electrically coupled to IMD 105 through a conductor extending within the lead body. The RA lead is shown placed in the atrial septum, but the RA lead may be placed in or near the atrial appendage, the atrial free wall, or elsewhere.

The example shown also includes a right ventricular (RV) lead 115 having a proximal end 117 and a distal end 119. The proximal end 117 is coupled to a header connector 107. The distal end 119 is configured for placement in the RV. The RV lead 115 may include one or more of a proximal defibrillation electrode 116, a distal defibrillation electrode 118, an RV tip electrode 120A, and an RV ring electrode 120B. The defibrillation electrode 116 is generally incorporated into the lead body such as in a location suitable for supraventricular placement in the RA and/or the superior vena cava. The defibrillation electrode 118 is incorporated into the lead body near the distal end 119 such as for placement in the RV. The RV electrodes 120A and 120B may form a bipolar electrode pair and are generally incorporated into the lead body at distal end 119. The electrodes 116, 118, 120A, and 120B are each electrically coupled to IMD 105, such as through one or more conductors extending within the lead body. The proximal defibrillation electrode 116, distal defibrillation electrode 118, or an electrode formed on the can of IMD 105 allow for delivery of cardioversion or defibrillation pulses to the heart.

The RV tip electrode 120A, RV ring electrode 120B, or an electrode formed on the can of IMD 105 allow for sensing an RV electrogram signal representative of RV depolarizations and delivering RV pacing pulses. In some examples, the IMD includes a sense amplifier circuit to provide amplification and/or filtering of the sensed signal. RA tip electrode 114A, RA ring electrode 114B, or an electrode formed on the can of IMD 105 allow for sensing an RA electrogram signal representative of RA depolarizations and allow for delivering RA pacing pulses. Sensing and pacing allows the IMD 105 to adjust timing of the heart chamber contractions. In some examples, the IMD 105 can adjust the timing of ventricular depolarizations with respect to the timing of atrial depolarizations by sensing electrical signals in the RA and pacing the RV at the desired atrial-ventricular (AV) delay time.

A left ventricular (LV) lead 125 can include a coronary pacing or sensing lead that includes an elongate lead body having a proximal end 121 and a distal end 123. The proximal end 121 is coupled to a header connector 107. A distal end 123 is configured for placement or insertion in the coronary vein. The LV lead 125 may include an LV ring or tip electrode 128A and an LV ring electrode 128B. The distal portion of the LV lead 125 is configured for placement in the coronary sinus and coronary vein such that the LV electrodes 128A and 128B are placed in the coronary vein. The LV electrodes 128A and 128B may form a bipolar electrode pair and are typically incorporated into the lead body at distal end 123. Each can be electrically coupled to IMD 105 such as through one or more conductors extending within the lead body. LV tip electrode 128A, LV ring electrode 128B, or an electrode formed on the can of the IMD 105 allow for sensing an LV electrogram signal representative of LV depolarizations and delivering LV pacing pulses.

An IMD may be configured with a variety of electrode arrangements, including transvenous, epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes).

As discussed previously, IMDs such as ICDs may detect tachyarrhythmia by first detecting a rapid heart rate. For example, a measured ventricular interval may be compared to a fixed VT detection threshold depolarization interval. Note that detection rates and detection intervals may be used interchangeably. For example, a detection rate 165 bpm is approximately equivalent to a detection interval of 360 ms.

When it's detected, VT can be terminated using high-energy shock therapy applied with an ICD, or using ATP therapy, or using a combination of both therapies. When the VT threshold rate is satisfied, IMDs may then apply other detection methods in addition to the fast rate detection to reduce the incidence of inappropriate shocks. For example, if the tachyarrhythmia is SVT, the programmed VT therapy can be inappropriate for SVT. When SVT is detected, the IMD may do nothing, or may apply pacing therapy to resolve the SVT.

Figure 2:
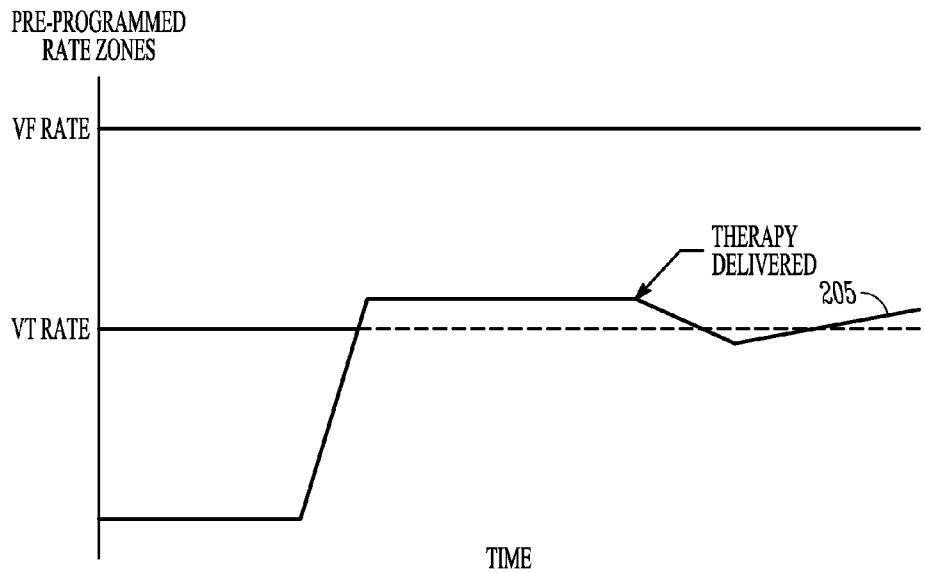
FIG. 2 shows an illustration of heart rate vs. time for a hypothetical episode of VT.

FIG. 2 shows an illustration of heart rate 205 vs. time for a hypothetical episode of VT. Two fixed threshold rates are shown, a VT detection threshold rate (VT Rate) and a VF detection threshold rate (VF Rate). VF is detected when the heart rate 205 exceeds the VF rate. Ventricular shock therapy is typically delivered for VF. VT is detected when the heart rate 205 exceeds the VT Rate. If the heart rate 205 exceeds a predetermined rate value (e.g., the VT Rate or another rate value) within a specified period of time, the detected rhythm may be classified as a sudden onset VT. After the heart rate exceeds the VT rate for a specified period of time, a therapy is delivered. The therapy may include ATP or high energy shock therapy. However, the delivered therapy may not work as desired. If the VT episode rate is near the detection threshold rate, the same VT episode may appear to an IMD to be two different episodes, which may lead to incorrect assumptions being made by the IMD about the VT episode.

For example, as shown in the FIG. 2, the rate may temporarily drop below the VT Rate after therapy is applied by an IMD. If the therapy is ineffective, the rate may again rise above the VT Rate. The IMD may incorrectly assume that this is a new episode of sudden onset VT. If the same therapy continues to be provided, and the therapy is ineffective, the IMD may detect the same VT episode as many VT episodes and continue to provide the ineffective therapy. A better approach to VT detection is to provide an adjustable VT detection threshold rate.

Figure 3:
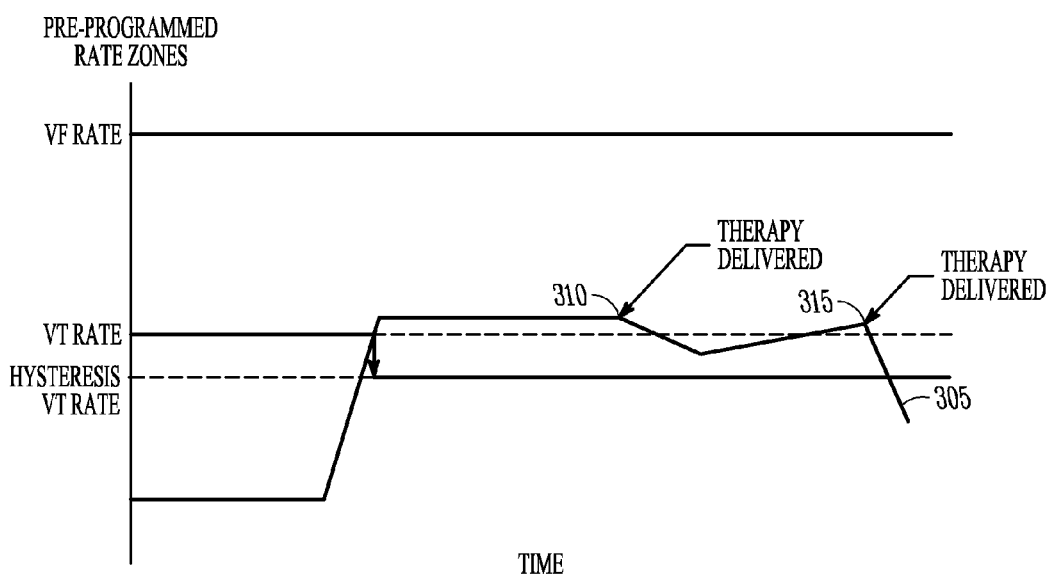
FIG. 3 shows another illustration of heart rate vs. time for a hypothetical episode of VT.

FIG. 3 shows another illustration of heart rate 305 vs. time for a hypothetical episode of VT. Sudden onset VT is again detected when the heart rate 305 exceeds a predetermined rate within a specified period of time. But in this example, when sudden onset VT is confirmed, a Hysteresis VT Rate is used to detect whether the VT episode is sustained or whether the episode has ended. The VT detection includes hysteresis because a first VT rate is used to detect VT, and a second lower VT rate is used to determine if the episode is sustained. If the detected rhythm is confirmed to be SVT, the VT detection threshold rate is unchanged. In certain examples, the VT detection threshold rate is increased when SVT is detected and confirmed.

After specified criteria are met following VT detection, a therapy is delivered at point 310. The specified criteria may include, among other things, a specified period of time, a specified number or specified percentage of beats classified as VT beats, or a combination of these criteria. As in FIG. 2, the rate may temporarily drop below the VT Rate after therapy is applied, but because the lower Hysteresis VT Rate is now being used to classify VT, the IMD declares that the same VT episode is continuing or persisting. This may cause the IMD to apply the next programmed therapy for the same episode at point 315, which can be a more aggressive therapy than the initial therapy. For example, the IMD may first try to convert the VT episode using ATP. Because of the lower Hysteresis VT Rate, the IMD knows that the previous therapy was ineffective and may apply high energy shock therapy. In some examples, the IMD may try ATP therapy a number of times, or try different ATP therapy regimens, before resorting to the shock therapy. Because the IMD has correctly declared the VT as one episode instead of numerous new episodes, the IMD makes appropriate therapy decisions.

It is important for the IMD to correctly classify the episode as sudden onset VT and not incorrectly classify an episode of SVT as VT. For SVT, the use of a Hysteresis VT Rate could result in delivery of an inappropriate therapy. An approach to determine whether a detected rhythm is VT or SVT is found in Kim et al., "Rhythm Discrimination of Sudden Onset and One-to-One Tachyarrhythmia," U.S. Patent Pub. No. 20070197928, filed on Feb. 17, 2006, which is incorporated by reference herein in its entirety, including its disclosure of VT/SVT discrimination.

Figure 4:
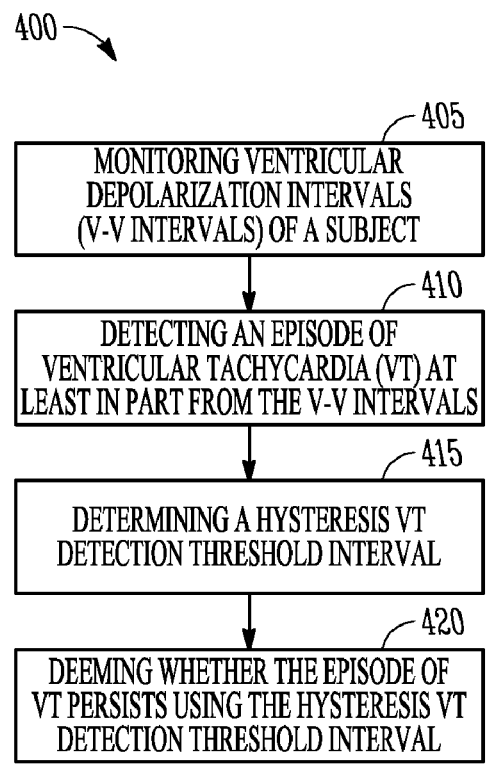
FIG. 4 shows a flow chart of an example of a method of detecting VT with a medical device.

FIG. 4 shows a flow chart of an example of a method 400 of detecting VT with a medical device. At block 405, ventricular depolarization intervals (V-V intervals) of a subject are monitored. At 410, an episode of VT is detected, at least in part, from the V-V intervals. At block 415, a hysteresis VT detection threshold interval is determined. At block 420, whether the episode of VT persists is deemed or declared using the hysteresis VT detection threshold interval.

Figure 5:
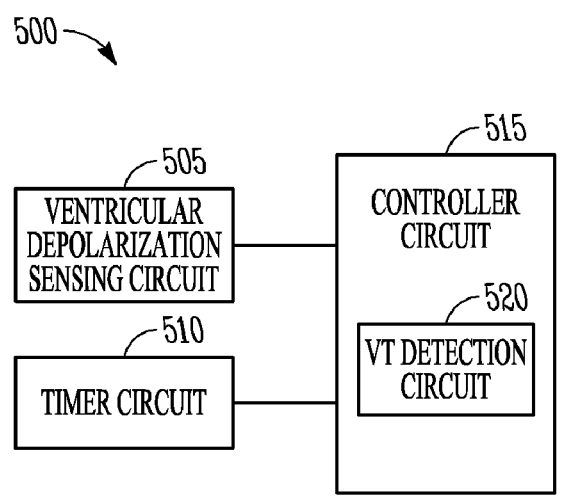
FIG. 5 is a block diagram of portions of an example of a device to detect VT.

FIG. 5 is a block diagram of portions of an example of a device 500 to detect VT. The device 500 includes an implantable ventricular depolarization sensing circuit 505 that provides a sensed ventricular depolarization signal. In some examples, the ventricular depolarization sensing circuit 505 includes a sense amplifier as described above regarding FIG. 1 communicatively coupled to electrodes (e.g., electrodes 120A and 120B). The device 500 also includes a timer circuit 510 configured to provide a ventricular depolarization time interval between V-V intervals and a controller circuit 515 communicatively coupled to the ventricular depolarization sensing circuit 505 and the timer circuit 510. The communicative coupling allows the controller circuit 515, the ventricular depolarization sensing circuit 505, and the timer circuit 510 to communicate using electrical signals even though there can be intervening circuitry between the controller circuit 515 and the sensing and timer circuits.

The controller circuit 515 can include a digital signal processor, application specific integrated circuit (ASIC), microprocessor, or other type of processor, interpreting or executing instructions in software or firmware. In some examples, the controller circuit 515 can include a state machine or sequencer that is implemented in hardware circuits. The controller circuit 515 can include any combination of hardware, firmware, or software.

The controller circuit 515 includes other circuits or modules to provide the functions described herein. These circuits can include software, hardware, firmware or any combination thereof. For example, the circuits can include instructions in software executing on, or interpreted by, the controller circuit 515. Multiple functions can be performed by one or more of the circuits.

The controller circuit 515 includes a VT detection circuit 520. The VT detection circuit 520 detects an episode of VT at least in part from the provided V-V intervals. In some examples, the VT detection circuit 520 detects VT when a threshold number of the V-V intervals are less than a fixed VT detection threshold interval, or when a ventricular depolarization rate determined from the V-V intervals exceeds a fixed VT detection threshold rate. As described below, the VT detection threshold may apply additional criteria to declare VT when the detection threshold is satisfied.

The VT detection circuit 520 also determines a hysteresis VT detection threshold interval. In some examples, the VT detection circuit 520 calculates the hysteresis VT detection threshold interval when a threshold number of the V-V intervals are less than the fixed VT detection threshold interval (e.g., sudden onset VT). Similarly, the VT detection circuit 520 may calculate the hysteresis VT detection threshold interval when a detected ventricular depolarization rate exceeds the fixed VT detection threshold rate.

The VT detection circuit 520 deems whether the episode of VT persists using the hysteresis VT detection threshold interval (or the rate corresponding to the threshold interval) instead of using the fixed VT detection threshold interval. In some examples, the VT detection circuit 520 is configured to determine the hysteresis VT detection threshold interval using a ventricular rate that is a specified rate value less than the VT detection threshold rate (e.g., 0.9 times the fixed VT detection threshold rate).

Figure 6:
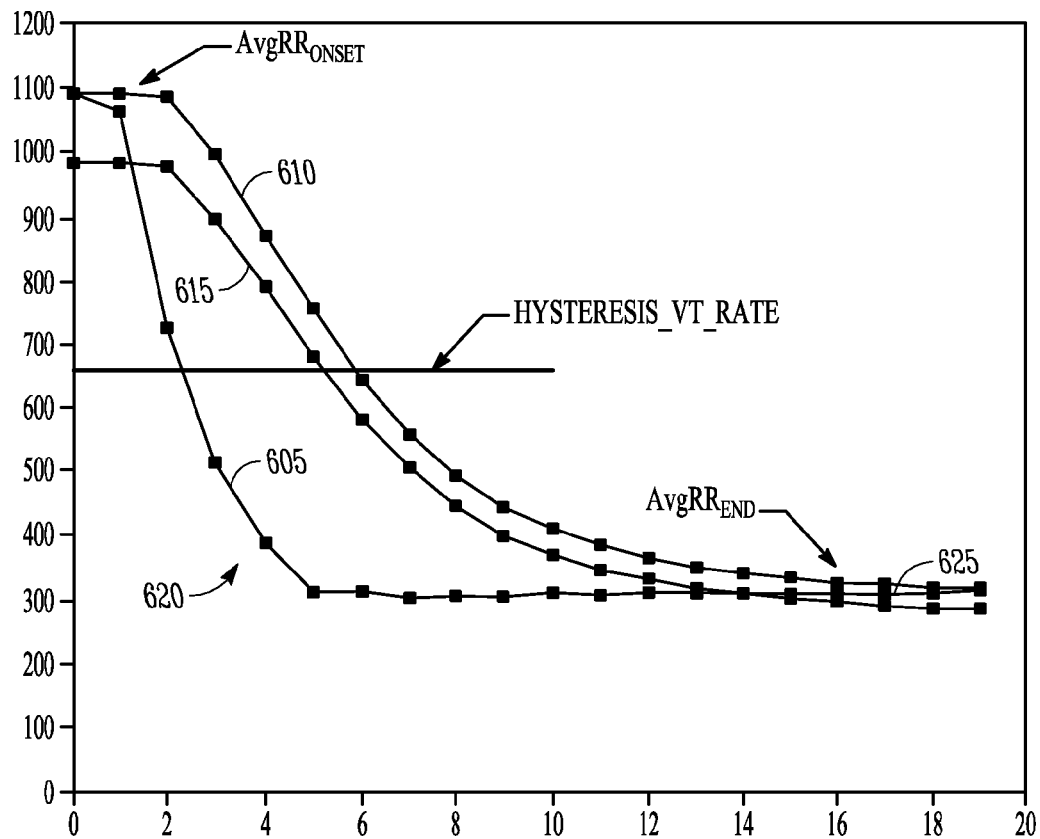
FIG. 6 shows an example of a graph of ventricular depolarization intervals vs. the corresponding heart beat number.

According to some examples, the VT detection circuit 520 calculates the hysteresis VT detection threshold interval using an accelerated beat interval. FIG. 6 shows an example of a graph of V-V intervals 605 (or RR intervals denoting R-wave to R-wave intervals where an R-wave is associated with depolarization of the ventricular chambers) vs. the corresponding heart beat number. The graph 605 illustrates a rapidly decreasing V-V interval or increasing heart rate. The FIG. also shows a graph of a central tendency (here, an average) of previous V-V intervals (AvgRR) 610 and a graph of 0.9 times AvgRR 615.

The VT detection circuit 520 classifies a V-V interval as an accelerated beat if the time interval has a shorter duration than a central tendency (e.g., an average) of previous V-V intervals (e.g., a V-V interval <0.9(AvgRR) is an accelerated beat). The VT detection circuit 520 also classifies a specified number of accelerated beat intervals (e.g., three consecutive accelerated beat intervals) as a sudden rate increase.

When the VT detection circuit 520 detects a sudden rate increase from the V-V intervals, the VT detection circuit 520 estimates or otherwise determines a VT onset interval. For example, the VT detection circuit 520 saves the AvgRR interval at the first accelerated beat interval as the onset average ventricular time interval ($AvgRR_{onset}$). In the example in FIG. 6, the third accelerated beat 620 and the $AvgRR_{onset}$ interval value are indicated.

After the sudden rate increase and when the VT detection circuit 520 detects a specified number of non-accelerated beats, the VT detection circuit estimates a VT end interval. For example, when the VT detection circuit 520 detects three non-accelerated beats, the VT detection circuit 520 saves the current AvgRR interval as the end average ventricular time interval ($AvgRR_{end}$). The third non-accelerated beat 625 and the $AvgRR_{end}$ interval value are indicated in FIG. 6. Note that the non-accelerated beat interval is defined by the 0.9 (AvgRR) curve and the non-accelerated beat interval is less than the first detected accelerated beat interval. The VT detection circuit calculates the hysteresis VT detection threshold interval between the onset average ventricular time interval and the end average ventricular time interval. In some examples, the hysteresis VT detection threshold interval is a central tendency of $AvgRR_{onset}$ and $AvgRR_{end}$, or $$\text{Hysteresis VT interval} = (AvgRR_{onset} + AvgRR_{end})/2.$$

Note that this calculation of the hysteresis VT detection threshold interval or rate does not depend on a fixed VT rate. One of ordinary skill in the art would understand, upon reading this detailed description, that other methods of determining the hysteresis VT detection threshold interval between $AvgRR_{onset}$ and $AvgRR_{end}$ are within the scope of this document. For example, the hysteresis VT detection threshold interval is the midpoint of $AvgRR_{onset}$ and $AvgRR_{end}$, or $$\text{Hysteresis VT interval} = ((AvgRR_{onset} - AvgRR_{end})/2 + AvgRR_{end}).$$

For a non-sustaining episode of VT, after a few accelerated beats, the V-V intervals may return to normal or near-normal intervals. When detected, the normal or near-normal intervals may be declared to be non-accelerated beats. In this case, the calculated hysteresis VT interval will be between the accelerated interval and the normal or near-normal interval, and the detected beats may be deemed to be non-VT beats during the non-sustaining episode.

In some examples, the VT detection circuit 520 declares VT in response to detecting a sudden rate increase without comparing a ventricular rate or time interval to a respective tachycardia detection rate or time interval threshold. Stated another way, the device 500 does not need a fixed VT detection threshold rate to declare VT, but instead declares a VT episode from a sudden rate increase that occurs within a specified time duration. Detection of VT from a sudden rate increase may be further qualified with having the ending heart rate being above some minimum rate criterion. The minimum rate criterion is deemed to be a minimum physiologic rate for classifying a rhythm as tachyarrhythmia (e.g., 90 bpm). Descriptions of systems, devices, and methods to detect tachyarrhythmia without a comparison to a specified lowest tachyarrhythmia rate are found in Kim et al., U.S. Patent Publication No. 20070135848, "Zoneless Tachyarrhythmia Detection with Real Time Rhythm Monitoring," filed Dec. 13, 2005, which is incorporated by reference herein in its entirety, including its disclosure of tachyarrhythmia detection systems, devices, and methods.

As stated previously, the VT detection circuit 520 may detect tachyarrhythmia by applying additional criteria to declare VT when a ventricular rate criterion is satisfied. A sudden high heart rate together with an assessment of V-V interval instability can be used to detect VT. In some examples, the VT detection circuit 520 determines a measure of ventricular rhythm stability using ventricular time intervals. Using the measure of ventricular rhythm stability, the VT detection circuit 520 determines that at least one of an episode of VT is detected or a VT episode persists. Examples of methods and systems to detect abnormal heart rhythms and assess the stability of the rhythms are found in Gilkerson et al., U.S. Pat. No. 6,493,579, entitled "System and Method for Detection Enhancement Programming," filed Aug. 20, 1999, which is incorporated herein by reference in its entirety, including its disclosure of detecting abnormal heart rhythms and assessing heart rhythm stability.

Figure 7:
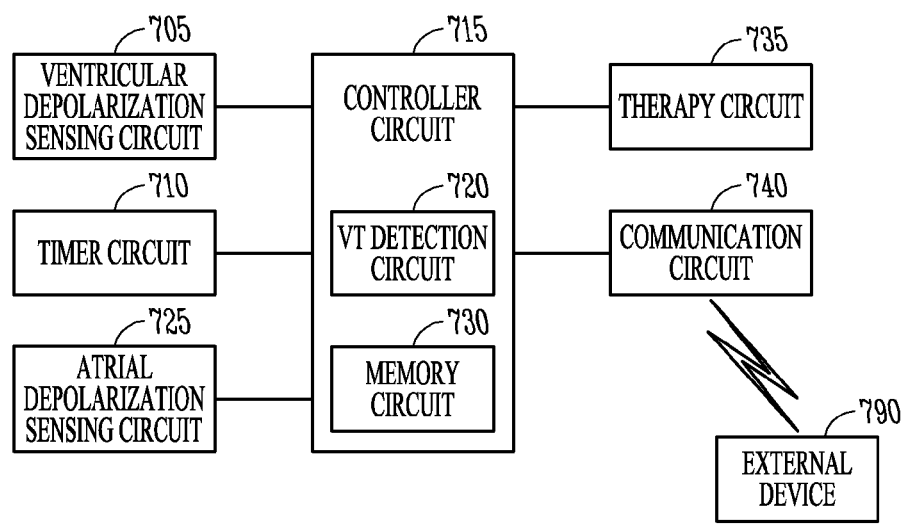
FIG. 7 is a block diagram of portions of another example of a device to detect VT.

FIG. 7 is a block diagram of portions of another example of a device 700 to detect VT. The device 700 includes an implantable ventricular depolarization sensing circuit 705, a timer circuit 710, and a controller circuit 715 that, in turn, includes a VT detection circuit 720 that determines a hysteresis VT detection threshold interval. In some examples, the device 700 includes an implantable atrial depolarization sensing circuit 725 that provides a sensed atrial depolarization signal. In some examples, the atrial depolarization sensing circuit 725 includes a sense amplifier communicatively coupled to implantable electrodes (e.g., electrodes 114A and 114B in FIG. 1). The timer circuit 710 provides an atrial time interval between atrial depolarizations.

The VT detection circuit 720 determines at least one of an occurrence of an episode of VT or the persistence of a VT episode, when an average ventricular depolarization rate exceeds an average atrial depolarization rate by more than a specified rate threshold value. For example, the ventricular depolarization may exceed a fixed VT threshold and the detected rhythm includes dissociation between the atrial and ventricular depolarizations. If the ventricular depolarization rate tracks, or nearly tracks, the atrial depolarization rate, or if the atrial depolarization rate exceeds the ventricular depolarization rate, then the episode is deemed to be SVT. A description of systems and methods that detect tachycardia using rate sensing channels is found in Gilkerson, et al., U.S. Pat. No. 6,522,925, "System and Method for Detection Enhancement Programming," filed May 13, 2000, which is incorporated herein by reference in its entirety, including its disclosure of systems and methods that detect tachycardia using rate sensing channels.

In some examples, after a possible VT episode is detected using rate, whether the episode is VT or SVT is then determined using the morphology of sensed cardiac signals. A proper characterization of a patient's supraventricular conducted rhythm (SVR) requires detection of unpaced or intrinsic heartbeats. Methods to characterize a patient's SVR are often dependent upon acquiring a sufficient number of intrinsic beats. Methods to characterize a patient's SVR are described in Kim et al., U.S. Pat. No. 6,708,058, entitled "Normal Cardiac Rhythm Template Generation System and Method," filed Apr. 30, 2001, which is hereby incorporated herein by reference in its entirety, including its description of systems and methods to characterize a patient's SVR. Another method is described in U.S. patent application Ser. No. 10/105,875, entitled "Method and System for Characterizing a Representative Cardiac Beat Using Multiple Templates," filed Mar. 25, 2002, which is hereby incorporated herein by reference in its entirety, including its description of systems and methods to characterize portions of heart signals using multiple templates.

In some examples, the device 700 includes a memory circuit 730 integral to or separate from the controller circuit 715. At least one area of the memory circuit 730 is allocated to store at least one of a normal sinus rhythm (NSR) template morphology or an SVR template morphology. Using a comparison of a morphology of a sensed cardiac signal to the stored template morphology, the VT detection circuit 720 determines that at least one of an episode of VT is detected or a VT episode persists. An approach to detecting tachyarrhythmia and to discriminating VT from SVT is described in Hsu et al., U.S. Pat. No. 6,889,081, entitled "Classification of Supraventricular and Ventricular Cardiac Rhythms Using Cross Channel Timing Algorithm," filed Jul. 23, 2002, which is incorporated herein by reference in its entirety, including its description of systems and methods for detecting tachyarrhythmia and for discriminating VT from SVT.

According to some examples, the device 700 includes a therapy circuit 735 communicatively coupled to the controller circuit 715. The therapy circuit 735 is configured to provide electrical anti-tachycardia therapy to the subject, such as ATP therapy and/or defibrillation/cardioversion shock therapy. The controller circuit 715 initiates ATP upon detecting and classifying the episode of VT, and initiates at least one of modified ATP or defibrillation/cardioversion shock therapy upon deeming that the episode of VT persists using the hysteresis VT detection threshold interval.

When an episode of VT occurs, it may be desirable to do one or both of report the episode to a clinician in order for the risks to the patient to be evaluated and alert the clinician with an indication of increased urgency. It may also be desirable to alert the clinician with increased urgency when an episode of VT persists for a long time. In some examples, the device 700 includes a communication circuit 740 communicatively coupled to the controller circuit 715. The communication circuit communicates with an external device 790 or system. In certain examples, the external device 790 includes an IMD programmer. In certain examples, the external device 790 is part of an advanced patient management (APM) system (e.g., a server). In certain examples, the external device 790 is a repeater to relay communications from the device 700 to a third device (e.g., a computer) communicatively coupled to an APM system.

Upon the VT detection circuit 720 deeming that the episode of VT persists longer than a specified time threshold using the hysteresis VT detection threshold interval, the controller circuit 715 communicates an indication of the episode of VT to the external device 790. Because the hysteresis VT detection threshold interval helps the VT detection circuit 720 to determine that the VT episode persists and is not multiple episodes, sustained episodes of VT may be more accurately reported by the device 700.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
    an implantable ventricular depolarization sensing circuit configured to provide a sensed ventricular depolarization signal;
    a timer circuit configured to provide a ventricular time interval between ventricular depolarizations; and
    a controller circuit communicatively coupled to the ventricular depolarization sensing circuit and the timer circuit, wherein the controller circuit includes a ventricular tachycardia (VT) detection circuit configured to:
        declare an episode of VT when a number of accelerated beats are detected, wherein an accelerated beat concludes a ventricular time interval having a shorter duration than a specified central tendency of previous ventricular time intervals;
        determine an estimated onset ventricular time interval using a value of at least one accelerated beat interval when the episode of VT is declared;
        determine an estimated end ventricular time interval using a value of at least one non-accelerated beat interval when a specified number of non-accelerated beat intervals are detected after the episode of VT is declared;
        calculate the hysteresis VT detection threshold interval using the estimated onset ventricular time interval and the estimated end ventricular time interval; and
        deem whether the episode of VT persists using the hysteresis VT detection threshold interval.

2. The apparatus of claim 1, wherein the VT detection circuit is configured to:
    determine a ventricular depolarization rate from ventricular time intervals;
    detect the episode of VT when the ventricular depolarization rate exceeds a VT detection threshold rate; and
    deem whether the episode of VT persists using a rate corresponding to the calculated hysteresis VT detection threshold interval instead of using the VT detection threshold rate.

3. The apparatus of claim 1, wherein the VT detection circuit is configured to first detect the episode of VT when a ventricular depolarization rate exceeds a VT detection threshold rate.

4. The apparatus of claim 1, including
    a memory circuit communicatively coupled to the controller circuit, wherein at least one area of the memory circuit is allocated to store at least one of a normal sinus rhythm (NSR) template morphology or a supraventricular conducted rhythm (SVR) template morphology, and
    wherein the VT detection circuit is configured to determine that at least one of an episode of VT is detected or a VT episode persists, using a comparison of a morphology of a sensed cardiac signal to the stored at least one of the NSR template morphology or the SVR template morphology.

5. The apparatus of claim 1, wherein the VT detection circuit is configured to:
    determine a measure of ventricular rhythm stability using ventricular time intervals; and
    determine, using the measure of ventricular rhythm stability, that at least one of an episode of VT is detected or a VT episode persists.

6. The apparatus of claim 1, including
    a therapy circuit communicatively coupled to the controller circuit, wherein the therapy circuit is configured to provide electrical anti-tachycardia therapy to a subject, and wherein the controller circuit is configured to:
        initiate anti-tachycardia pacing (ATP) upon detecting the episode of VT; and
        initiate at least one of modified ATP or defibrillation cardioversion shock therapy upon deeming that the episode of VT persists using the hysteresis VT detection threshold interval.

7. The apparatus of claim 1, including
    a communication circuit, communicatively coupled to the controller circuit, configured to communicate with an external device, and
    wherein the controller circuit is configured to communicate an indication of the episode of VT to an external device upon deeming, using the hysteresis VT detection threshold interval, that the episode of VT persists longer than a specified time threshold.

8. The apparatus of claim 1, including
    a therapy circuit communicatively coupled to the controller circuit, wherein the therapy circuit is configured to provide at least one of defibrillation shock therapy and cardioversion shock therapy to a subject, and wherein the controller circuit is configured to initiate a shock therapy upon detecting the episode of VT.

9. An apparatus comprising:
    an implantable ventricular depolarization sensing circuit configured to provide a sensed ventricular depolarization signal;
    a timer circuit configured to provide a ventricular time interval between ventricular depolarizations; and
    a controller circuit communicatively coupled to the ventricular depolarization sensing circuit and the timer circuit, wherein the controller circuit includes a VT detection circuit configured to:
        declare an episode of VT when a number of accelerated beats are detected, wherein an accelerated beat concludes a ventricular time interval having a shorter duration than a specified central tendency of previous ventricular time intervals;

determine an onset central tendency ventricular time interval using a value of a running central tendency beat interval when VT is declared;

determine an end central tendency ventricular time interval using the value of the running central tendency beat interval when a specified number of non-accelerated beat intervals are detected after the VT is declared; and calculate a hysteresis VT detection threshold interval that is between the onset central tendency ventricular time interval and the end central tendency ventricular time interval; and deem whether the episode of VT persists using the hysteresis VT detection threshold interval.

10. The apparatus of claim 9, wherein the hysteresis VT detection threshold interval is an average of an onset average ventricular time interval and an end average ventricular time interval.

11. An apparatus comprising:

an implantable ventricular depolarization sensing circuit configured to provide a sensed ventricular depolarization signal;

a timer circuit configured to provide a ventricular time interval between ventricular depolarizations; and a controller circuit communicatively coupled to the ventricular depolarization sensing circuit and the timer circuit, wherein the controller circuit includes a VT detection circuit is configured to:

declare VT in response to detecting a sudden heart rate increase, without comparing a ventricular rate or time interval to a respective tachycardia detection rate or time interval threshold, wherein the sudden rate increase includes a specified number of accelerated beats occurring within a specified time period, wherein an accelerated beat concludes a ventricular time interval having a shorter duration than a specified central tendency of previous ventricular time intervals;

calculate a hysteresis VT detection threshold interval using an accelerated beat interval and a non-accelerated beat interval, wherein the non-accelerated beat interval is detected after VT is declared; and deem whether the episode of VT persists using the hysteresis VT detection threshold interval.

12. An apparatus comprising:

an implantable atrial depolarization sensing circuit configured to provide a sensed atrial depolarization signal;

an implantable ventricular depolarization sensing circuit configured to provide a sensed ventricular depolarization signal;

a timer circuit configured to provide an atrial time interval between atrial depolarizations and provide a ventricular time interval between ventricular depolarizations; and a controller circuit communicatively coupled to the ventricular depolarization sensing circuit and the timer circuit, wherein the controller circuit includes a VT detection circuit configured to:

declare an episode of VT when a number of accelerated beats are detected, wherein an accelerated beat concludes a ventricular time interval having a shorter duration than a specified central tendency of previous ventricular time intervals;

determine that at least one of an episode of VT is detected or a VT episode persists, when an average ventricular depolarization rate exceeds an average atrial depolarization rate by more than a specified rate threshold value;

calculate a hysteresis VT detection threshold interval using an accelerated beat interval and a non-accelerated beat interval, wherein the non-accelerated beat interval is detected after VT is declared; and deem whether the episode of VT persists using the hysteresis VT detection threshold interval.

13. A method of operating an implantable medical device, the method comprising:

monitoring ventricular depolarization intervals (V-V intervals), between successive ventricular depolarizations, of a subject using the implantable medical device;

declaring an episode of ventricular tachyarrhythmia (VT) at least in part from a number of detected accelerated beats, wherein an accelerated beat is a ventricular time interval having a shorter duration than a specified central tendency of previous V-V intervals;

determining an onset central tendency V-V interval using at least one accelerated beat interval;

determining an end central tendency V-V interval using at least one non-accelerated beat interval that occurs a specified number of non-accelerated beat intervals after detecting the specified number of accelerated beats;

determining a hysteresis VT detection threshold interval that is between the onset central tendency V-V interval and the end central tendency V-V interval; and generating an indication of whether the episode of VT persists using the hysteresis VT detection threshold interval.

14. The method of claim 13, wherein declaring an episode of VT includes:

using a fixed VT detection threshold rate to detect the episode of VT; and detecting a ventricular depolarization rate in the V-V intervals that is within a specified range of the fixed VT detection threshold rate, and wherein the method includes using the hysteresis VT detection threshold interval, instead of the fixed VT detection threshold rate, to declare whether the episode of VT persists.

15. The method of claim 13, including:

wherein declaring an episode of VT includes detecting a sudden rate increase in the V-V intervals without comparing a ventricular rate or time interval to a respective tachycardia detection rate or time interval detection threshold, wherein the sudden rate increase includes a specified number of accelerated beats, and wherein an accelerated beat is a V-V interval having a shorter duration than an average of previous V-V intervals; and wherein determining the hysteresis VT detection threshold interval includes calculating the hysteresis VT detection threshold interval using at least one accelerated beat interval.

16. The method of claim 13, wherein determining the hysteresis VT detection threshold interval includes determining a hysteresis VT detection threshold interval that is an average of an onset average ventricular time interval and an end average ventricular time interval.

17. The method of claim 13, including:

providing ATP upon detecting the episode of VT; and providing at least one of modified ATP or defibrillation cardioversion shock therapy upon deeming that the episode of VT persists using the hysteresis VT detection threshold interval.

18. The method of claim 13, including communicating an indication of the episode of VT to an external device upon deeming, using the hysteresis VT detection threshold interval, that the episode of VT persists longer than a specified time threshold.

19. The method of claim 13, wherein declaring an episode of VT includes declaring an episode of sudden onset VT, and wherein the method includes deeming whether the episode of sudden onset VT persists using the hysteresis VT detection threshold interval.

20. A method of operating an implantable medical device, the method comprising:
monitoring ventricular depolarization intervals (V-V intervals), between successive ventricular depolarizations, of a subject using the implantable medical device;
declaring an episode of ventricular tachyarrhythmia (VT) at least in part from a number of detected accelerated beats, wherein an accelerated beat is a ventricular time interval having a shorter duration than a specified central tendency of previous V-V intervals; wherein declaring an episode of VT also includes at least one of:
determining that an average ventricular depolarization rate exceeds an average atrial depolarization rate by more than a specified rate threshold value;
comparing a morphology of a sensed cardiac signal to a template morphology; or
assessing stability of the ventricular rhythm:
determining a hysteresis VT detection threshold interval using an accelerated beat interval and non-accelerated beat interval, wherein the non-accelerated beat interval is detected after VT is declared; and
generating an indication of whether the episode of VT persists using the hysteresis VT detection threshold interval.

21. A method of operating an implantable medical device, the method comprising:
monitoring ventricular depolarization intervals (V-V intervals), between successive ventricular depolarizations, of a subject using the implantable medical device;
declaring an episode of ventricular tachyarrhythmia (VT) at least in part from a number of detected accelerated beats, wherein an accelerated beat is a ventricular time interval having a shorter duration than a specified central tendency of previous V-V intervals;
determining a hysteresis VT detection threshold interval using an accelerated beat interval and non-accelerated beat interval, wherein the non-accelerated beat interval is detected after VT is declared; and
generating an indication of whether the episode of VT persists using the hysteresis VT detection threshold interval including deeming whether the episode of VT persists using at least one of:
determining that an average ventricular depolarization rate exceeds an average atrial depolarization rate by more than a specified rate threshold value;
comparing a morphology of a sensed cardiac signal to a template morphology; or
assessing stability of the ventricular rhythm.

* * * * *